United States Patent [19]

Olbrich et al.

[11] Patent Number: 5,082,987
[45] Date of Patent: Jan. 21, 1992

[54] TREATMENT OF HYDROCARBONS

[75] Inventors: Michael E. Olbrich, Naperville, Ill.; Rebecca L. Jones, West Columbia, Tex.; Roger W. Fenstermaker, Bartlesville, Okla.

[73] Assignee: Phillips Petroleum Company, Bartlesville, Okla.

[21] Appl. No.: 597,932

[22] Filed: Oct. 15, 1990

[51] Int. Cl.$^5$ .................. C07C 5/13; C07C 7/12; B01J 20/34
[52] U.S. Cl. .................. 585/737; 585/820; 585/854; 585/826; 502/31
[58] Field of Search .............. 585/737, 820, 854, 826; 502/31

[56] References Cited

U.S. PATENT DOCUMENTS

| | | | |
|---|---|---|---|
| 2,376,060 | 5/1945 | Jones | 585/737 |
| 2,376,078 | 5/1945 | Oberfell et al. | 585/737 |
| 3,540,998 | 11/1970 | Bercik et al. | 585/737 |
| 3,760,029 | 9/1973 | McCoy | 585/737 |
| 4,562,300 | 12/1985 | LaFoy | 585/854 |

Primary Examiner—Anthony McFarlane
Assistant Examiner—Nhat Phan
Attorney, Agent, or Firm—Charles W. Stewart

[57] ABSTRACT

Method and apparatus are described whereby a caustic-treated hydrocarbon feed mixture having a contaminating concentration of water and sulfur compounds is treated by separating the hydrocarbon feed into a first stream and a second stream. The first stream is contacted with an adsorbent material to produce a reactor feed stream having a significant reduction in the concentration of the contaminating water and sulfur compounds. The reactor feed stream is thereafter contacted in the presence of hydrogen under suitable isomerization conditions with an isomerization catalyst to produce an isomerate product.

4 Claims, 1 Drawing Sheet

TREATMENT OF HYDROCARBONS

FIELD OF THE INVENTION

This invention relates to the treatment of hydrocarbon-containing feedstreams. The invention further relates to the removal of water and sulfur compounds from a hydrocarbon-containing feedstream prior to isomerization of said hydrocarbon-containing feedstream so as to improve reaction activity of the isomerization catalyst and conversion of the normal hydrocarbons within the hydrocarbon-containing feedstream to their corresponding isomers.

The isomerization of paraffin hydrocarbons having from 4 to 6 carbon atoms is practiced to create more highly branched isomers from the normal or straight-chain hydrocarbons. One purpose of an isomerization process is to provide high octane blend components for refined gasoline. The isomers can also be used in the production of other products or used as solvents. For the isomerization of normal butane, it is generally desired to produce an isobutane product that can be used as a feedstock in the manufacture of methyl tertiary butyl ether (MTBE) or in the manufacture of an alkylate product produced by the alkylation of isobutane with olefin hydrocarbon compounds. The isomerization of pentane, hexane, and refinery light naphtha mixtures is also practiced in order to produce high octane gasoline blending components. The isomerization of normal or straight-chain hydrocarbons can significantly improve the overall octane number of the gasoline pool produced from petroleum refining operations.

In the isomerization of paraffin hydrocarbons, it is desirable to isomerize a hydrocarbon-containing feedstream that contains a minimum amount of sulfur compounds and water because of their contaminating effects upon the isomerization catalyst. Generally, water serves as a poison to isomerization catalysts, and sulfur compounds act as temporary poisons that inhibit catalyst isomerization activity. The larger the concentration of water and sulfur compounds within a hydrocarbon-containing stream, the lower the attainable conversion per pass of the normal hydrocarbons to their corresponding isomer compounds, consequently resulting in lower product yields.

Recent developments in the process for producing linear low density polyethylene have resulted in the requirement that an extremely high purity, essentially contaminant-free isopentane product be utilized as a solvent. Generally, this high purity isopentane requires that its sulfur content be less than 1 part per million by weight (ppmw) and that the water content be less than 10 ppmw. Because of the more rigorous product specification for isopentane that is to be used in the production of linear low density polyethylene, it becomes more difficult and more costly to produce. While there are a number of commercial processes which can be used for the production of this high purity product, many of them are costly to operate and involve high initial capital costs.

There are many methods known in the art for removing water and sulfur compounds from hydrocarbon-containing feedstreams. One such process involves the caustic treating of a hydrocarbon stream to remove sulfur compounds as is described in U.S. Pat. No. 4,562,300 and the references cited therein. One difficulty with the caustic treating method referred to above is that disulfide compounds are produced which have a slight solubility in the hydrocarbon-containing stream being treated and, because of this slight solubility, small quantities of disulfide compounds remain in the treated hydrocarbon-containing stream. Due to the slight concentration of disulfide compounds in the treated hydrocarbon-containing stream when it is charged to an isomerization reaction zone, the isomerization catalyst activity is inhibited resulting in a lower conversion and lower product yield. Therefore, the removal of the small quantities of contaminating sulfur compounds from the hydrocarbon-containing feedstream prior to charging the feedstream to an isomerization reaction zone can substantially improve catalyst activity and conversion. Additionally, the removal of the disulfide compounds from the treated hydrocarbon-containing stream prior to charging the stream to an isomerization reactor can result in providing a high purity isomerate that contains minimal quantities of sulfur compounds.

It is, therefore, an object of this invention to provide an improved method and apparatus for removing contaminating quantities of water and sulfur compounds from hydrocarbon-containing streams.

A further object of this invention is to provide method and apparatus for enhancing the activity of isomerization catalyst in order to improve the conversion of straight-chain hydrocarbons to their corresponding branched chain isomers and to increase product yield.

A still further object of this invention is to provide method and apparatus for producing at low cost a treated hydrocarbon-containing stream suitable for isomerization.

Another object of this invention is to provide a method for producing an essentially contaminant-free, high purity isomerate product suitable for use in the production of linear low density polyethylene.

SUMMARY OF THE INVENTION

Thus, the method of the present invention relates to treating a caustic-treated hydrocarbon feed mixture having a contaminating concentration of water and sulfur compounds by separating the caustic-treated hydrocarbon feed mixture into a first stream comprising normal pentane and heavier hydrocarbon compounds and a second stream comprising isopentane and lighter hydrocarbon compounds. The first stream is contacted with a molecular sieve material to absorb water and sulfur compounds from the first stream and thereby produce a reactor feed stream having a significant reduction in the concentration of water and sulfur compounds contained therein. The reactor feed stream is thereafter contacted in the presence of hydrogen under suitable isomerization conditions with an isomerization catalyst to produce an isomerate product stream.

Another aspect of the present invention includes apparatus for treating a caustic-treated hydrocarbon feed mixture having a contaminating concentration of water and sulfur compounds comprising first separating means for separating the caustic-treated hydrocarbon feed mixture into a first stream comprising normal pentane and heavier hydrocarbon compounds and a second stream comprising isopentane and ligher hydrocarbon compounds. A significant reduction in the concentration of water and sulfur compounds in the first stream is achieved by contacting means for contacting said first stream with a molecular sieve material to produce a reactor feed stream. An isomerate stream is produced by utilizing isomerizing means for isomerizing the reactor feed stream by contacting said reactor feed stream in the presence of hydrogen under suitable isomerization conditions with an isomerization catalyst.

Other aspects, objects and advantages of this invention will become apparent from the study of this disclosure, appended claims, and the drawing in which:

DETAILED DESCRIPTION OF THE INVENTION

Figure 1:
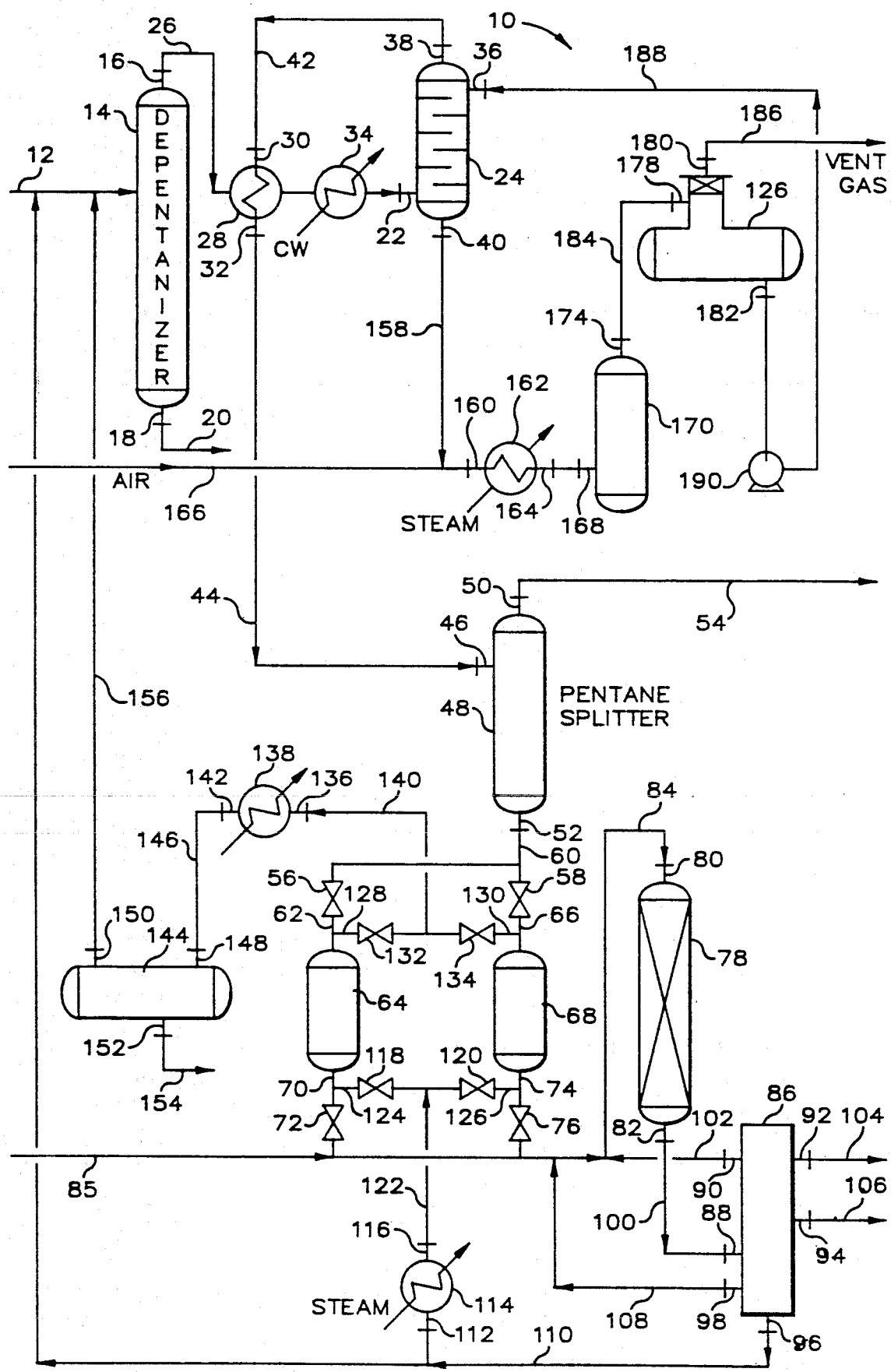
FIG. 1 is a schematic representation of a process for treating and isomerizing a hydrocarbon feed mixture that includes the features of the novel invention.

Processes for the isomerization of normal hydrocarbons to their corresponding branched compounds or isomers are generally equilibrium-type processes in which the amount of conversion of normal paraffins to branched structures are limited by thermodynamic equilibrium factors. In most isomerization processes, it is desirable for the isomerization reactions to take place at the lowest achievable temperatures because the conversion of normal paraffins to their corresponding branched structures generally increases as the reaction temperatures are decreased. To achieve greater conversion of normal paraffins to their corresponding isomers, high activity isomerization catalysts are used which improve the reaction rate of isomerization reactions at low reaction temperatures. One difficulty encountered with the use of isomerization catalysts is that they are usually very sensitive to the presence of water and sulfur compounds. Generally, the presence of water in the reactor feed and the presence of sulfur compounds in the reactor feed work as poisons to the catalyst thereby inhibiting isomerization catalyst activity. The presence of these contaminants has the effect of lowering the attainable conversion of the normal paraffins to their branched isomers and decreasing product yield. While sulfur compounds are often temporary poisons to the catalyst, it is still desirable to minimize the amount of sulfur compounds contained in an isomerization reactor feed material because of the improvement in conversion and yield that are achievable by lowering the concentration of sulfur.

The inventive process utilizes a caustic treating step to remove a significant presence of mercaptan type sulfur compounds from a hydrocarbon feedstream prior to isomerization and to convert remaining sulfur compounds to mainly disulfides, which can be separated from the hydrocarbon feedstream by simple separation methods such as by fractionation. Prior to caustic treating of the hydrocarbon feedstream, a hydrocarbon feed mixture from which the feed material for isomerization is taken passes through a separation step whereby the paraffin hydrocarbons desired for isomerization are separated as an overhead stream from other hydrocarbons that are not desirable for isomerization, which are recovered as a bottoms product stream.

Any suitable hydrocarbon feed mixture can be utilized in this invention. Such suitable hydrocarbon feed mixtures can include hydrocarbon distillates, gasoline, which includes cracked gasoline, straight-run gasoline or mixtures thereof, naphtha, jet fuel, kerosene, and hydrocarbons having at least 4 carbon atoms. The preferred hydrocarbon feed mixture is a hydrocarbon stream containing hydrocarbons having at least 4 carbon atoms, but most preferred, the hydrocarbon stream should comprise a pentane mixture.

In order to maintain a high isomerization catalyst activity, it is desirable that there be no sulfur compounds contained within the hydrocarbon feed mixture. The inventive features of this invention have been developed for the purpose of removing at least a significant portion of the sulfur compounds contained within the hydrocarbon feed mixture prior to charging a particular portion of the hydrocarbon feed mixture to an isomerization reaction zone. Generally, the hydrocarbon feed mixture will be a sour hydrocarbon stream containing significant quantities of sulfur compounds with the concentration of such compounds ranging upwardly to about 2 weight percent, or more. While the type of sulfur compounds can vary significantly, the compounds that are generally present are mercaptans, sulfides, disulfides, and thiophenes.

Prior to the treating of a hydrocarbon feed mixture stream to remove a significant portion of the contaminating sulfur compounds contained therein, the hydrocarbon feed mixture stream can optionally undergo a separation step. In this separation step, the lighter hydrocarbons, which are the more preferred isomerization feed materials, are separated from the heavier hydrocarbons. It is generally preferred to separate hydrocarbons having less than 7 carbon atoms from those hydrocarbons having more than 6 carbon atoms. The most preferred split of the hydrocarbon feed mixture stream is to separate the hydrocarbons having less than 6 carbon atoms from those hydrocarbons having more than 5 carbon atoms.

Any suitable means for separating the hydrocarbons can be used. Many of the various separating means known in the art are disclosed at length in *Perry's Chemical Engineers' Handbook*, (6th edition, 1984) and can include conventional distillation methods, liquid-liquid extraction methods, adsorption processes, and such novel processes as those that use permeable membranes for separation. The preferred separation means, however, is the use of conventional distillation methods. The separated hydrocarbon stream, which consists essentially of hydrocarbons having less than 7 carbon atoms, or preferably less than 6 carbon atoms, is fed to caustic treating means for the removal of sulfur compounds to produce a caustic-treated hydrocarbon feed mixture. There are many known and suitable methods for caustic treating hydrocarbon streams for the purpose of removing contaminating levels of sulfur compounds. One such suitable method comprises contacting a hydrocarbon stream with an alkaline solution that comprises water and an alkaline reagent. The solution can be regenerated by a catalyzed reaction of sulfur compounds, which generally are organic sulfur compounds such as mercaptans, to disulfides and a subsequent separation of the thus formed disulfides from the solution. For reference, suitable caustic treating means are throughly described in U.S. Pat. No. 4,562,300 and in the references cited therein.

The alkaline solution composition generally is an aqueous solution with the alkaline present in the range generally from about 5 to about 50 weight percent, but preferably in the range of from about 10 to about 15 weight percent. The preferred caustic material is an aqueous solution of sodium hydroxide in water. Other materials such as potassium hydroxide and lithium hydroxide in aqueous solution can be used.

The alkaline solution is contacted with the hydrocarbon feedstream in a countercurrent extractor. This extraction process takes place at temperatures in the range of from about 100° F. to about 150° F. and pressures in the range of from about 60 psig to about 110 psig. Preferably, the temperature in the extractor will be about 125° F., and the pressure will be about 85 psig. The weight ratio of feed to alkaline solution fed into the extractor should range from about 2.0 to about 4.0. In the contactor, mercaptans such as methyl mercaptan and isopropyl mercaptan are removed to form RSNa and water where R is an alkyl group.

The contacting apparatus can be chosen from any common contacting apparatus, but it is preferably a countercurrent liquid-liquid trayed contactor. This apparatus preferably contains perforated trays. The alkaline solution can flow, for example, from the top to the bottom of the apparatus countercurrently to the hydrocarbon feed. The treated hydrocarbon feedstream leaves the extractor and can be further treated and separated through conventional means.

The contacted alkaline solution exits from the extractor and is then injected into an oxygenation reactor. In the oxygenation reactor, the mercaptans are oxygenated to disulfides. A catalyst can also be used in the oxygenation reactor. The thus formed organic disulfides are insoluble in the aqueous alkaline solution. Some of the sulfur materials will remain unreacted from the oxygenation reactor. This stream is then sent to a settler to separate the disulfides from the alkaline stream.

The mercaptan rich alkaline solution is heated to the temperature range of from about 145° F. to about 150° F. prior to feeding the solution to the oxygenation reactor. Air is injected and the flow is cocurrent in the oxygenation reactor, which can be any conventional reactor, but preferably is a packed column containing one inch diameter Raschig rings. The pressure in the oxygenation reactor will range from about 70 to about 75 psig.

After the oxygenation step, the alkaline and sulfur material are passed to a phase separator where alkaline solution containing upwardly to about 60 ppmw, or more, total organic sulfides and disulfides are separated from an organic disulfide phase.

In most instances, the above-described caustic treating means provides an effective removal of the organic sulfur compounds that are contained within hydrocarbon feed mixture streams; however, because of the solubility of disulfide compounds in hydrocarbon mixtures and because of the less than complete removal of sulfur compounds from a hydrocarbon feed mixture, the caustic-treated hydrocarbon feed mixture can contain a concentration of sulfur compounds. Furthermore, because the contacting solution utilized in caustic treating means is an aqueous solution, the caustic-treated hydrocarbon feed mixture will be saturated with water and potentially will have quantities of free water suspended therein. The sulfur concentration can range upwardly to about 150 ppmw and the water concentration can range upwardly to about 200 ppmw. Generally, the sulfur concentration in the caustic-treated hydrocarbon feed mixture stream will range from about 40 ppmw to about 150 ppmw and the water concentration will range from about 100 ppmw to about 200 ppmw.

The caustic-treated hydrocarbon feed mixture can optionally be separated into a first stream and a second stream prior to contacting of at least a portion of the caustic-treated hydrocarbon feed mixture with an adsorbent material to produce a product stream having a significant reduction in the concentration of the water and sulfur compounds contained therein. The separating means can be any suitable means for splitting the caustic-treated hydrocarbon feed mixture stream into a first stream and a second stream, but it is preferable that conventional distillation means be utilized as a part of this invention. It is preferred that the first stream from separating means comprise that portion of the caustic-treated hydrocarbon feed mixture comprising normal alkane hydrocarbons having at least 4 carbon atoms. In the more preferred embodiment of this invention, the caustic-treated hydrocarbon feed mixture will comprise primarily normal pentane and isopentane, and separating means will separate or split the normal pentane and isopentane into the two streams with the first stream comprising essentially that portion of the caustic-treated hydrocarbon feed mixture that is normal pentane and with the second stream comprising essentially that portion of the caustic-treated hydrocarbon feed mixture that is isopentane. The sulfur compounds and water contained within the caustic-treated hydrocarbon feed mixture will concentrate essentially in the first stream.

The first stream is contacted by contacting means with an adsorbent material used for removing the sulfur compounds and water present in the first stream. Any suitable adsorbent can be used, but the preferred adsorbent is a molecular sieve material of the crystalline form having a uniform pore diameter of less than about 10 angstroms (Å). Suitable molecular sieve materials are described in the art and include commercially available molecular sieves such as Zeolite A, X, L, Y, mordenite, montmorillonite, baroid clays, and the like. Other suitable adsorbents may include supported nickel and molybdenum oxide and zinc oxide. The preferred molecular sieve material for use in this invention and for removing the water and sulfur compounds from the first stream is the material known in the trade as type 13X. A type 13X molecular sieve is generally effective for adsorbing molecules having diameters of less than 10 Å and excluding molecules having diameters of greater than 10 Å. The type 13X molecular sieve material will have a nominal pore diameter of about 10 Å and will come in a form having a bulk density in the range of from about 25 to about 45 pounds per cubic foot.

It is generally desirable that by contacting the first stream with an adsorbent material, a significant reduction in the amount of sulfur compounds and water contained within the first stream is achieved to produce a suitable isomerization reactor feed stream or reactor feed stream. Preferably, the amount of sulfur compounds and water adsorbed by the adsorbent material will be such that the concentration of sulfur compounds in the reactor feed stream is less than 1 ppmw and the concentration of water in the reactor feed stream is less than 10 ppmw. However, the concentration of sulfur compounds contained in the reactor feed stream can range upwardly to about 150 ppmw and the concentration of water in the reactor feed stream can range upwardly to about 200 ppmw.

The reactor feed stream, having a significant reduction in the concentration of the water and sulfur compounds, is fed to an isomerization reaction zone wherein the reactor feed stream is contacted in the presence of hydrogen under suitable isomerization conditions with an isomerization catalyst to produce an isomerization reactor product or reactor effluent or isomerate stream.

The isomerization of normal alkane hydrocarbons is generally accomplished in the vapor phase at reaction conditions including a temperature in the range of from about 300° F. to about 800° F. and preferably in the range of from 475° F. to 575° F. The pressure in the reaction zone is generally in the range of from about 300 psig to about 900 psig and preferably in the range of from 300 psig to 500 psig. The hourly space velocity will fairly depend upon the operating temperature and pressure and preferably will be in the range of from about 0.1 hour$^{-1}$ to about 10 hours$^{-1}$, and more preferably, from about 0.5 hour$^{-1}$ to about 5 hours$^{-1}$. The term "hourly space velocity" refers to the number of reactor volumes of feed at standard conditions of one atmosphere and 60° F. which is treated per hour. The values for hourly space velocity are determined by the ratio of volumetric flow rate at standard conditions and in terms of hours to the reactor volume.

The isomerization of the normal alkanes is performed in the presence of hydrogen. Hydrogen is generally present in an amount of from about 0.1 to about 10 moles of hydrogen per mole of feed, and preferably from 0.5 to 5 moles of hydrogen per mole of feed. The presence of hydrogen favorably improves the conversion of n-butane and n-pentane to isobutane and isopentane, respectively. Furthermore, the presence of hydrogen in the reaction zone helps reduce the formation of coke which tends to poison the isomerization catalyst. The hydrogen is recovered from the effluent from the isomerization reactor and preferably purified and recycled to the reaction zone. The hydrogen to the reaction zone may thus consist solely of recycle hydrogen or a mixture of recycle hydrogen and make-up hydrogen or, simply, make-up hydrogen. Generally, however, a recycle stream is used in the isomerization process.

Best isomerization results are obtained with the use of substantially pure n-butane or n-pentane or mixtures thereof. Thus, preferably the feeds will be at least 90 percent n-butane or n-pentane or mixtures thereof. However, the isomerization process can also be conducted with feeds, which, besides the n-butane or n-pentane hydrocarbons, or mixtures thereof, contain certain amounts of other hydrocarbons. While the admixture of large percentages of heavier hydrocarbons, such as naphtha, has a damaging effect on the process or cause reactions which inhibit or suppress the isomerization of the n-butane or n-pentane, or mixtures thereof, it is possible to have small percentages of such higher hydrocarbons with n-butane or n-pentane, or mixtures thereof.

The isomerization catalyst used in this invention can be any suitable catalyst composition that provides for the equilibrium isomerization of normal alkane hydrocarbons. Examples of such suitable isomerization catalyst compositions are described in J. J. McKetta and W. A. Cunningham, *Encyclopedia of Chemical Processing and Design*, volume 27, pages 444-447, Marcel-Dekker, Inc., 1988. A preferred isomerization catalyst comprises a platinum group component in association with a porous solid carrier.

The porous solid carrier is a porous inorganic oxide and preferably a high surface area inorganic oxide, for example, an inorganic oxide having a surface area of from about 50 to about 700 m$^2$/gm and preferably from 100 to 700 m$^2$/gm. Satisfactory porous solid carriers for the preparation of the catalyst for use in the process of the invention include silica, zirconia, magnesia, thoria, alumina, and the like, and combinations thereof, for example, silica-alumina, silica-zirconia, alumina-silica-magnesia, alumina-thoria, alumina-thoria-zirconia, and the like.

Alumina is a particularly suitable carrier or support for the catalyst used in the present invention. Furthermore, alumina can be prepared by a variety of methods for purposes of this invention. Thus, the alumina can be prepared by adding a suitable alkaline agent such as ammonium hydroxide to a salt of aluminum, such as, aluminum chloride, aluminum nitrate, and the like, in an amount to form aluminum hydroxide that upon drying and calcining is converted to alumina. Alumina may also be prepared by the reaction of sodium aluminate with a suitable reagent to cause precipitation thereof with the resulting formation of aluminum hydroxide gel. Also, alumina may be prepared by the reaction of metallic aluminum with hydrochloric acid, acetic acid, and the like, in order to form a hydrosol which can be gelled with a suitable precipitating agent, such as, ammonium hydroxide, followed by drying and calcination.

The most preferred carriers for the support of the platinum group catalyst are molecular sieve materials as previously described herein.

The platinum group component catalyst should contain a platinum group component in an amount of from about 0.01 to about 3 weight percent and preferably in an amount from 0.1 to 1 weight percent based on the finished catalyst. The platinum group component embraces all the members of Group VIII of the Periodic Table having an atomic weight greater than 100 as well as compounds and mixtures of any of these. Thus, the platinum group components are the Group VIII noble metals or compounds thereof. Platinum is preferred because of its better performance in isomerization reactions. Regardless of the form in which the platinum group component exists on the catalyst, whether as metal or compound, the weight percent is calculated as the metal.

The platinum group component is associated with the porous solid carrier by various methods. The platinum group component can be disposed on the carrier by a suitable technique such as ion-exchange, impregnation, coprecipitation, and other similar methods. Generally, it is preferred that the platinum group component be associated with the porous solid carrier by impregnation. The impregnation is generally accomplished with an aqueous solution of a decomposable compound of a platinum group metal in sufficient concentration to provide the desired quantity of the platinum group component on the finished catalyst. Preferred platinum group compounds include chloroplatinic acid, ammonium chloroplatinates, polyammineplatinum salts, palladium chloride, iridium chloride, chloroiridic acid, and the like.

Various promoters can optionally be incorporated with the platinum group components to increase the activity, stability, and other characteristics of the catalyst. Metal promoters as, for example, rhenium, may be added. Also, combinations of one platinum group component with another platinum group component, such as, for example, platinum and iridium, can be used.

Halides, particularly fluoride or chloride, may be used to promote the catalyst for isomerization of n-butane and/or n-pentane. Chloride is the preferred halide. The halides apparently provide a limited amount of acidity to the catalyst which is beneficial to most isomerization reactions. A catalyst promoted with halide preferably contains from about 0.1 to about 10 weight percent, more preferably 3 to 6 weight percent. The halide can be incorporated onto the catalyst at any suitable stage of catalyst manufacture, for example, prior to or following incorporation of the platinum group component. Some halide is often incorporated with the catalyst by impregnation with the platinum group component; that is, for example, impregnation with chloroplatinic acid normally results in chloride addition to the catalyst. Additional halide may also be incorporated with the catalyst, if desired. In general, the halides are combined with the catalyst by contacting a suitable compound, such as, hydrogen fluoride, ammonium fluoride, hydrogen chloride, ammonium chloride, either in the gaseous form or in a water soluble form with the catalyst. Preferably, the fluoride or chloride is incorporated with the catalyst from an aqueous solution containing the halide.

Typically, the isomerate stream is passed to a separation system whereby the isomerate stream is separated into a recycle hydrogen stream, a stream of light hydrocarbons and hydrogen, a stream comprising the desirable isomer, and a recycle stream comprising the unconverted normal paraffin. Additionally, a heavy recycle stream, comprising compounds having relative volatilities lower than that of the unconverted normal paraffin in the recycle stream, can also be provided for by the separation means.

A common arrangement for the separation system is to feed the isomerate stream to product separator means in which a gas phase and a liquid phase are separated. The gas phase comprises primarily hydrogen, which is recycled to be mixed with the reactor feed stream and, preferably, with a combined reactor feed and recycle stream prior to charging the thus formed mixture to the isomerization reactor. As for the liquid phase from product separator means, it is generally charged to stabilizer separation means whereby the lighter hydrocarbons and the remaining hydrogen that is dissolved in the liquid is separated from a hydrocarbon mixture comprising the desired alkane isomer, the unconverted normal alkane, and the heavy recycle stream compounds. This hydrocarbon mixture is then fed to fractionator separation means whereby a split between the desired isomer and a mixture of the unconverted normal paraffin and heavy recycle stream compounds is made. Generally, an overhead stream from fractionator separation means contains the desired isomer and a bottoms stream will contain essentially those compounds having a relative volatility lower than that of the desired isomer. A preferred embodiment of the invention will provide a medial stream or sidedraw stream used as the recycle stream comprising primarily the unconverted normal paraffin, and the bottoms stream is used as the heavy recycle stream.

The preferred embodiment of the invention is to provide the separation system to separate the isomerate stream into at least a third stream, a fourth stream and a fifth stream. The fourth stream, which comprises primarily the unconverted normal alkane feed to the isomerization reactor, can preferably be recycled to be mixed with the reactor feed stream prior to charging the thus formed mixture to the isomerization reactor. As an optional feature of this invention, the fourth stream or a portion of such stream may be fed to storage. The fifth stream comprises primarily at least a portion of the heavy compounds of the isomerate stream, which have relative volatilities lower than that of the unconverted normal paraffin compounds. The fifth stream is preferably recycled and mixed with the hydrocarbon feed mixture prior to the thus formed mixture undergoing the earlier mentioned separation step whereby the heavy compounds are removed along with the earlier described heavier hydrocarbons. At least a portion of the fifth stream can be utilized, either on a continuous basis or an intermittent basis, to regenerate the earlier described adsorbent when it is spent.

Because it is frequently necessary to regenerate the adsorbent material, a feature of this invention includes the use of at least a portion of the fifth stream as a purge stream to regenerate the adsorbent material. It is generally necessary to regenerate the adsorbent material on a cyclic basis with the regeneration cycle times ranging upwardly to as often as every 24 hours or longer. The regeneration of the adsorbent material is accomplished by purging at elevated temperatures with at least a portion of the fifth stream. Preferably, the regeneration is accomplished by passing the heated at least a portion of said fifth stream through the bed of adsorbent material. The purging is generally performed until a very limited amount of water and sulfur compounds are evident in the exiting regeneration purge stream. Suitably, regeneration is conducted at a temperature of from about 200° F. to about 600° F. In order to maintain frequent regeneration of the adsorbent material, it can be desirable to have several parallel adsorbent beds so that as one is removed for regeneration others may be used for adsorption; thus, a continuous process can be maintained.

The regeneration purge stream can be mixed with the incoming hydrocarbon feed mixture in the same manner as is the fifth stream.

DETAILED DESCRIPTION OF THE DRAWING

Referring now to FIG. 1, there is provided a schematic representation of a hydrocarbon treating system 10 for a preferred embodiment of the invention. Conduit 12 shown provides for fluid flow to a medial section of depentanizer fractionator column or depentanizer 14 which has an overhead outlet 16 and a bottoms outlet 18. Conduit 20 is operably connected with bottoms outlet 18 for conveying fluid from depentanizer 14. Providing for fluid flow communication between overhead outlet 16 and bottom inlet 22 of countercurrent extractor 24 is conduit 26 which is operably connected between overhead outlet 16 and bottom inlet 22 for conveying fluid from depentanizer 14 to countercurrent extractor 24. Interposed in conduit 26 are heat exchanger 28, having an inlet 30 and an outlet 32, and heat exchanger 34.

Countercurrent extractor 24 is additionally provided with a top inlet 36, an overhead outlet 38 and a bottoms outlet 40. Conduit 42 is operably connected between overhead outlet 38 and inlet 30 to provide for fluid flow communication from countercurrent extractor 24 to heat exchanger 28. Conduit 44 is operably connected between outlet 32 and inlet 46 of pentane fractionator column or pentane splitter 48 to provide for fluid flow communication from heat exchanger 28 to pentane splitter 48. Pentane splitter 48 is additionally provided with an overhead outlet 50 and a bottoms outlet 52. Conduit 54 is operably connected to overhead outlet 50 for converging fluid from pentane splitter 48.

Providing for fluid flow communication between bottoms outlet 52 and the inlet to valves 56 and 58 is conduit 60. Conduit 62 provides for fluid flow communication between the outlet of valve 56 and dryer vessel 64 and conduit 66 provides for fluid flow communication between the outlet of valve 58 and dryer vessel 68. Conduit 70 provides for fluid flow communication between dryer vessel 64 and the inlet of valve 72, and conduit 74 provides for fluid flow communication between dryer vessel 68 and the inlet of valve 76. Fluid flow communication between the outlets of valves 72 and 76 and isomerization reactor vessel 78, which has an inlet 80 and an outlet 82, is provided for by conduit 84 that is operably connected between valves 72 and 76 and inlet 80. Fluid can be conveyed from dryer vessels 64 and 68 to isomerization reactor vessel 78 via conduit 84. Operably connected to conduit 84 is conduit 85 which provides for fluid flow to conduit 84.

For separating a fluid into five separate fluid streams is separation system 86 having an inlet 88, a first outlet 90, a second outlet 92, a third outlet 94, a fourth outlet 96 and a fifth outlet 98. Conduit 100 is operably connected between outlet 82 and inlet 88 for conveying fluid from isomerization reactor vessel 78 to separation system 86. For conveying fluid from separation system 86 to conduit 84 is conduit 102 which is operably connected between first outlet 90 and conduit 84. Conduits 104 and 106 are operably connected to second outlet 92 and third outlet 94, respectively, for conveying fluid from separator system 86. For conveying fluid from separation system 86 to conduit 84 is conduit 108 which is operably connected between fifth outlet 98 and conduit 84.

For recycling fluid from separator system 86, conduit 110 is provided. Conduit 110 is operably connected between fourth outlet 96 and conduit 12 and inlet 112 of heat exchanger 114 for conveying fluid from separator system 86 to either heat exchanger 114 or conduit 12, or both. Heat exchanger 114 is also equipped with outlet 116. Providing for fluid flow communication between outlet 116 and the inlets of valves 118 and 120 is conduit 122 which is operably connected between outlet 116 and the inlet of valves 118 and 120. Conduits 124 and 126 are respectively connected to the outlets of valves 118 and 120. For conveying fluid from valves 118 and 120 to dryer vessels 64 and 68, respectively, conduit 124 is operably connected between the outlet of valve 118 and conduit 70 and conduit 126 is operably connected between the outlet of valve 120 and conduit 74.

For removing fluid from dryer vessels 64 and 68 are conduits 128 and 130. Conduit 128 is operably connected between conduit 62 and the inlet of valve 132 for conveying fluid from dryer vessel 64 to valve 132. Conduit 130 is operably connected between conduit 66 and the inlet of valve 134 for conveying fluid from dryer vessel 68 to valve 134. For conveying fluid from the outlets of valves 132 and 134 to inlet 136 of heat exchanger 138 is conduit 140 which is operably connected between the outlets of valves 132 and 134 and inlet 136. Heat exchanger 138 is additionally provided with outlet 142.

For conveying fluid from heat exchanger 138 to separation vessel 144 is conduit 146. Separation vessel 144 is equipped with a top inlet 148, a top outlet 150 and a bottom outlet 152. Conduit 146 is operably connected between outlet 142 and top inlet 148 for conveying fluid from heat exchanger 138 to separation vessel 144. Operably connected to bottom outlet 152 is conduit 154 for conveying fluid from separation vessel 144. Providing for fluid flow communication between conduit 12 and separation vessel 144 is conduit 156 which is operably connected between top outlet 150 and conduit 12.

Conduit 158 is operably connected between bottoms outlet 40 and inlet 160 of heat exchanger 162 for conveying fluid from countercurrent extractor 24 to heat exchanger 162 which is provided with an inlet 160 and an outlet 164. Conduit 166 is operably connected to conduit 158 to provide for fluid flow to conduit 158. Operably connected between outlet 164 and bottom inlet 168 of oxygenation reactor 170 is conduit 172. Oxygenation reactor 170 is provided with bottom inlet 168 and overhead outlet 174 for allowing fluid flow through oxygenation reactor 170.

Fluid flow communication between settler separator 176, having an inlet 178, an overhead outlet 180, and a bottoms outlet 182, is provided for by conduit 184 which is operably connected between overhead outlet 174 and inlet 178. Conduit 186 is operably connected to overhead outlet 180 for conveying fluid from settler separator 176. Conduit 188 is connected between bottoms outlet 182 and top inlet 36 for conveying fluid from settler separator 176 and countercurrent extractor 24. Interposed in conduit 188 is pump 190 for imparting energy head to the fluid passing through conduit 188.

In operating hydrocarbon treating system 10, a hydrocarbon feed mixture is charged to hydrocarbon treating system 10 through conduit 12. It is preferred that the hydrocarbon feed mixture comprise primarily hydrocarbons having at least 5 carbon atoms. The hydrocarbon feed mixture is charged to depentanizer 14 which defines a separation zone and provides means for separating the hydrocarbon feed mixture. In depentanizer 14, the hydrocarbon feed mixture will be separated into two streams, one comprising primarily pentane and lighter compounds, which is the overhead of depentanizer 14 that passes through conduit 26, and the bottoms product stream, which comprises primarily cyclopentane and heavier compounds, that passes by way of conduit 20 to storage or to further downstream processing.

The pentane and lighter hydrocarbons pass by way of conduit 26 to countercurrent extractor 24 which defines a contacting zone and provides means for caustic treating the pentane and lighter hydrocarbons. Optionally, the pentane and lighter stream can exchange heat with certain heat transfer mediums by use of heat exchangers 28 and 34 which provide means for the indirect exchange of heat between the pentane and lighter stream and heat transfer mediums. Within countercurrent extractor 24, the pentane and lighter hydrocarbons are contacted in a countercurrent fashion with a caustic composition such as an alkaline solution. In the presently preferred case where the alkaline solution is sodium hydroxide in an aqueous phase, most of the mercaptan compounds contained within the hydrocarbon stream will be removed in the form of water and RSNa, where R is an alkyl group. The thus caustic-treated hydrocarbons will pass by way of conduit 44 to pentane splitter 48 which provides means for separating the caustic-treated hydrocarbons into an overhead stream comprising primarily isopentane and a bottoms stream comprising primarily normal pentane. Optionally, the caustic-treated hydrocarbon mixture can pass through heat exchanger 28 to exchange heat with the pentane and lighter hydrocarbons being charged to countercurrent extractor 24 via conduit 26.

The contacted alkaline solution exits countercurrent extractor 24 through conduit 158 to oxygenation reactor 170. Within oxygenation reactor 170, the mercaptans contained within the alkaline solution are converted into insoluble organic disulfide compounds by reacting the compounds with an oxygen-containing gas, such as air. Air is injected into the solution via conduit 166. The thus formed organic disulfides and aqueous solution pass by way of conduit 184 to settler separator 176, which defines a separation zone and provides means for separating at least a substantial portion of the organic disulfides and other organic sulfur compounds from the alkaline solution. The thus separated alkaline solution, having a significant reduction in the concentration of organic disulfides and organic sulfur compounds, is recycled through conduit 188 to countercurrent extractpr 24 wherein it is used as the alkaline solution for contacting with the pentane and lighter hydrocarbons entering countercurrent extractor 24 via conduit 26.

Pentane splitter 48 defines a separation zone and provides means for separating the caustic-treated hydrocarbons into an overhead stream and a bottoms product stream. Preferably, the overhead stream comprises primarily isopentane and lighter compounds that pass by way of conduit 54 to either storage or for further downstream processing. The bottoms product stream comprises primarily normal pentane and heavier hydrocarbon compounds, water and sulfur compounds, which include disulfides, that can be present in the caustic-treated hydrocarbon feed mixture. The normal pentane and heavier hydrocarbon stream, laden with the water and sulfur compounds, passes by way of conduit 60, valve 58 and conduit 66 to dryer vessel 68. Alternatively, the normal pentane and heavier hydrocarbon stream can pass by way of conduit 60, valve 56 and conduit 62 to dryer vessel 64. The desired fluid flow direction can be controlled by maintaining either valve 56 or valve 58 in the closed position. Dryer vessels 64 and 68 define a contacting zone and provide means for contacting the normal pentane and heavier hydrocarbon stream with an adsorbent material to remove water and sulfur compounds from the normal pentane and heavier hydrocarbon stream and produce a reactor feed stream. The preferred adsorbent material contained within dryer vessels 64 and 68 is the molecular sieve adsorbent material previously described herein.

The desired fluid flow through either dryer vessel 64 or dryer vessel 68 is controlled by maintaining either valve 72 or valve 76, in cooperation with valves 56 and 58, in a closed position. Following is an example to illustrate the operation of dryer vessels 64 and 68. If it is desired to pass the bottoms product stream of pentane splitter 48 through dryer vessel 68, valves 56 and 72 are kept in the closed position to block the flow of pentane splitter 48 bottoms product stream through dryer vessel 64. Valves 58 and 76, on the other hand, are maintained in the open position to permit the flow of pentane splitter 48 bottoms product stream through dryer vessel 68. Alternatively, if it is desired to pass the bottoms product stream of pentane splitter 48 through dryer vessel 64, valves 58 and 76 are kept in the closed position to block fluid flow through dryer vessel 68 and valves 56 and 72 are maintained in the open position to permit fluid flow through dryer vessel 64.

The reactor feed stream from either dryer vessel 64 or dryer vessel 68 passes by way of conduit 84 to isomerization reactor 78 wherein it is contacted with an isomerization catalyst, as earlier described herein, contained within isomerization reactor vessel 78 to produce an isomerate stream or isomerization reactor effluent. Isomerization reactor vessel 78 defines a reaction zone and provides means for isomerizing the reactor feed stream from either dryer vessel 64 or dryer vessel 68 or, alternatively, contacting the reactor feed stream with the isomerization catalyst. The isomerate stream passes by way of conduit 100 to separation system 86 which defines a separation zone and provides for separating the isomerate stream into at least four separate streams but, preferably, into at least five separate streams. In separation system 86, the isomerate stream is separated into a stream comprising butane and lighter hydrocarbons that passes from separator system 86 by way of conduit 104 for downstream processing or use, a stream comprising primarily isopentane that passes from separator system 86 by way of conduit 106 for downstream use or storage, a recycle stream comprising primarily normal pentane that passes from separator system 86 by way of conduit 108 to be mixed with the reactor feed stream flowing through conduit 84 prior to charging the mixture to isomerization reactor vessel 78, a recycle hydrogen stream that passes from separator system 86 by way of conduit 102 to be mixed with the reactor feed stream flowing through conduit 84 prior to the feeding the thus formed mixture to isomerization reactor vessel 78, and a heavy recycle stream comprising cyclopentane and heavier components that is recycled from separation system 86 via conduit 110.

At least a portion of the heavy recycle stream passing through conduit 110 can be recycled to conduit 12 to be mixed with the incoming hydrocarbon feed mixture prior to feeding the thus formed mixture to depentanizer 14. Additionally, at least a portion of the heavy recycle stream passing from separation system 86 by way of conduit 110 can be utilized as a purge stream to regenerate the adsorbent material contained within dryer vessels 64 and 68. Heat exchanger 114 is used to provide heat exchange means for heating the regeneration purge stream prior to feeding it to either dryer vessel 64 or dryer vessel 68 to regenerate the molecular sieve material contained within the vessels. In operating dryer vessels 64 and 68, preferably, one dryer vessel will be undergoing a regeneration cycle while the other vessel is simultaneously undergoing a contacting or adsorption cycle. For example, if dryer vessel 64 is undergoing a regeneration cycle and dryer vessel 68 is undergoing a contacting cycle, valves 58, 76, 118, and 132 will be in the open position and valves 56, 72, 120 and 134 will be in the closed position. These valve positions will result in directing the purge stream through dryer vessel 64 to regenerate the molecular sieve material contained in dryer vessel 64, and the valve positions will result in directing the bottoms stream from pentane splitter 48 through dryer vessel 68 to be contacted with the molecular sieve material contained therein. To alternate the fluid flows, the valve positions are reversed thus completing a regeneration-contacting cycle.

The hot purge stream passing through the adsorbent materials within either dryer vessel 64 or dryer vessel 68, passes as a regenerative effluent stream by way of conduit 140 to a separation vessel 144 which defines a separation zone and provides separation means whereby the water that is removed from the adsorbent material is separated from the hydrocarbon that is in said regeneration effluent stream. Heat exchanger 138 provides heat exchange means for removing heat from the regeneration effluent stream in order to condense the hydrocarbon and water stream passing through conduit 140. The water separated in separation vessel 144 passes by way of conduit 154 to downstream disposal and the separated hydrocarbon from separation vessel 144 passes by way of conduit 156 to conduit 12 wherein it is mixed with the incoming hydrocarbon feed mixture to form a hydrocarbon feedstream which is charged to depentanizer 14. The sulfur compounds and the remaining unremoved water purged from the adsorbent materials contained in dryer vessels 64 and 68 are ultimately removed with the bottoms product stream of depentanizer 14 via conduit 20.

The hereindescribed invention provides for the efficient removal of contaminating quantities of water and sulfur compounds from hydrocarbon-containing streams. Because the resultant reduced levels of contaminating sulfur compounds and water in the isomerization reaction zone feed, a significant improvement in the conversion of straight chain hydrocarbons to their corresponding branched chain isomers can be achieved. By utilizing the method and apparatus described, a high purity isopentane product suitable for use in the production of linear low density polyethylene can be economically produced.

While the invention has been described in terms of the presently preferred embodiment, reasonable variations and modifications are possible by those skilled in the art. Such variations and modifications are within the scope of the described invention and the appended claims.

That which is claimed is:

1. A method of treating a caustic-treated hydrocarbon feed mixture having a contaminating concentration of water and sulfur compounds comprising the steps of:
   (a) separating said caustic-treated hydrocarbon feed mixture into a first stream, comprising normal pentane and heavier hydrocarbon compounds and a second stream comprising isopentane and lighter hydrocarbon compounds;
   (b) contacting said first stream with a molecular sieve material to adsorb water and sulfur compounds from said first stream and thereby produce a reactor feed stream having a significant reduction in the concentration of said water and sulfur compounds;
   (c) isomerizing said reactor feed stream by contacting said reactor feed stream in the presence of hydrogen under suitable isomerization conditions with an isomerization catalyst to produce an isomerate stream comprising isopentane, normal pentane, butane and lighter hydrocarbons, and cyclopentane and heavier hydrocarbons;
   (d) separating said isomerate stream into at least a third stream comprising cyclopentane and heavier hydrocarbons, a fourth stream comprising butanes and lighter hydrocarbons, a fifth stream comprising normal pentane, and a sixth stream comprising isopentane;
   (e) regenerating said molecular sieve material by contacting at least a portion of said molecular sieve material under conditions suitable for removing at least a significant portion of said water and sulfur compounds adsorbed by said molecular sieve material during step (b) with a regeneration purge stream comprising at least a portion of said third stream to produce a regeneration effluent stream comprising said regeneration purge stream and at least a portion of the water and sulfur compounds from said molecular sieve material; and
   (f) withdrawing said regeneration effluent stream from said molecular sieve material.

2. A method as recited in claim 1 further comprising the steps of:
   separating water from said regeneration effluent stream to produce a dewatered effluent stream; and
   mixing said dewatered regeneration effluent stream with a hydrocarbon feed mixture having a contaminating concentration of sulfur compounds to produce a mixed hydrocarbon feed stream.

3. A method as recited in claim 2 further comprising the steps of:
   separating said mixed hydrocarbon feed stream into an overhead stream and a bottoms product stream; and
   contacting said overhead stream with a caustic composition to remove sulfur compounds to thereby produce said caustic-treated hydrocarbon feed mixture.

4. A method as recited in claim 3 wherein said caustic-treated hydrocarbon feed mixture is formed by the step of:
   contacting said overhead stream with an alkaline solution to thereby remove at least a portion of said sulfur compounds contained in said overhead stream.

* * * * *